United States Patent [19]

Song et al.

[11] Patent Number: 5,126,456

[45] Date of Patent: Jun. 30, 1992

[54] 7-CHLOROQUINALDINE SYNTHESIS

[75] Inventors: Zhiguo Song, Edison; David L. Hughes, Old Bridge, both of N.J.

[73] Assignee: Merck & Co., Inc., Rahway, N.J.

[21] Appl. No.: 777,979

[22] Filed: Oct. 17, 1991

[51] Int. Cl.$^5$ .......................................... C07D 215/18
[52] U.S. Cl. .................................................. 546/180
[58] Field of Search ........................................ 546/180

[56] References Cited

U.S. PATENT DOCUMENTS 2,507,146  5/1950  Dickey ............................... 546/180

FOREIGN PATENT DOCUMENTS 0063386  6/1978  Japan ................................. 546/180
395063   2/1933  United Kingdom ................ 546/180

OTHER PUBLICATIONS

W. P. Utermohlen, Jr., J. Org. Chem., 1943, 8, 544.
C. M. Leir, J. Org. Chem., 1977, 42, 911.
A. M. Speivey et al., J. Chem., Soc., 1949, 2656.

*Primary Examiner*—David B. Springer
*Attorney, Agent, or Firm*—Gabriel Lopez; Joseph F. DiPrima

[57] ABSTRACT

An improved process is described which utilizes tetrachloro-1,4(or 1,2)-quinone as an oxidant in the Doebner-Miller synthesis of 7-chloroquinaldine, a starting material in the preparation of leukotriene antagonists. The process improves yield and eliminates the need of forming a $ZnCl_2$ complex to isolate the end product.

6 Claims, No Drawings

7-CHLOROQUINALDINE SYNTHESIS

BACKGROUND OF THE INVENTION

The Doebner-Miller reaction (Doebner et al., Ber., 14, 2816 (1881)) has been used for the preparation of substituted quinaldines for over 100 years. However, low yields and purification problems have led to many investigations of improved syntheses. Among these are: Utermohlen, J. Org. Chem., 8, 544 (1943); Spivey et al, J. Chem. Soc., 2656 (1949); and Leir, J. Org. Chem., 42, 911 (1977).

U.S. Pat. No. 4,851,409 teaches the preparation of substituted quinaldines using $ZnCl_2$ to precipitate the end product, as described by Leir. U.S. Pat. No. 4,851,409 is incorporated herein by reference for its teaching of the use of 7-chloroquinaldine as a starting material for the preparation of 2-substituted quinoline dioic acids which are antagonists of leukotriene and useful as anti-asthma drugs.

SUMMARY OF THE INVENTION

An improved process has now been found for the preparation of 7-chloroquinaldine. The process is run under non-aqueous conditions and uses tetrachloro-1,4(or 1,2)-quinone (p(or o)-chloranil) as an oxidant in the Doebner-Miller reaction. The process improves yields, improves the ratio of 7-chloroquinaldine to 5-chloroquinaldine, and eliminates the need for formation of a zinc chloride complex in the isolation of the end product.

DETAILED DESCRIPTION OF THE INVENTION

The process comprises reacting, in a non-aqueous medium, 3-chloroaniline with crotonaldehyde in alcohol under mineral acid, preferably HCl, catalysis in the presence of chloranil and then isolating the product as the acid (e.g., HCl) salt, as by crystallization. Most conveniently, the acidified alcohol is used as the reaction medium.

The alcohols used in the process are $C_2$-$C_4$ alcohols such as ethanol, propanol, isopropanol, n-butanol, isobutanol, and t-butanol, and preferably 2-butanol.

The reaction is run under moderate temperatures (75°-110° C.). Isolation can be started in less than 1 hour after crotonaldehyde addition is completed.

Yield is improved if crotonaldehyde addition is slow (0.5-2 hours), preferably with good stirring of the reaction mixture.

Reagent concentrations are conveniently in the range of 0.5-2M; acid concentrations range from 1.5-8M. Equimolar amounts of the aniline and chloranil, and a slight excess of crotonaldehyde are used.

The invention is further defined by reference to the examples, which are intended to be illustrative and not limiting. Temperatures are in degrees Celsius.

EXAMPLE 1

7-Chloroquinaldine

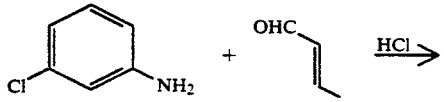

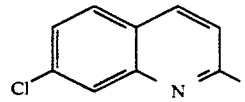

Step 1

Preparation of HCl in 2-Butanol

HCl gas was bubbled into 400 mL ice-cooled 2-butanol for 10 min. (exothermic, temperature increased to ~50°-60° C.) to a final concentration of 4.6N, concentration was assayed by removing 10 mL of solution, cooled to room temperature, diluting the sample to 100 mL with DI water, and titrating with 10 mL 0.995N NaOH solution. The titration was followed with a pH meter to an end point of pH=7.0.

Step 2

To a 2 L 3-neck flask equipped with a stirrer and a reflux condenser was added 3-chloroaniline (60.0 g, 470 mmol), 2-butanol (396 mL), HCl solution in 2-butanol (4.6N, 204 mL, total 2-butanol=600 mL) with stirring (exothermic, temperature increased to ~50° C.). Then p-chloranil solid (115.6 g, 470 mmol) was added. A 250 mL addition funnel was mounted to the flask and charged with crotonaldehyde (40.0 g, 571 mmol) and 2-butanol (120 mL). The mixture in the flask was stirred and heated to reflux (103° C.), and the crotonaldehyde solution was added dropwise and with efficient stirring over 50 min. The solid, yellow p-chloranil reacted and the mixture turned dark gradually.

The mixture was refluxed for an additional 20 min. and cooled to ~50° C. Then under vacuum, ~360 mL of the solvent was distilled while the mixture was stirred (b.p. 55°-65° C./10 cm Hg). Then 720 mL of was added under atmospheric pressure and 720 mL of solvent was distilled under vacuum (b.p. 55°-65° C./10 cm Hg). Then, under atmospheric pressure, 720 mL THF was added and the mixture refluxed for 30 min before it was cooled to 0° C. and left at 0° C. for 2 hours. The solid, which also contains some 5-chloro isomer by-product, was collected by filtration and washed with 8×100 mL THF.

The wet cake was transferred to a 2 L 3-neck round bottom flask equipped with a reflux condenser, a stirrer, and an addition funnel. 160 mL methanol was added and heated to reflux to dissolve all the solid. Then 720 mL THF was added through the addition funnel slowly over 45 min. The mixture was refluxed for 30 min., cooled to 0° C., and left to stand at 0° C. for one hour. The solid was collected by filtration and washed with 4×100 mL THF (until the washing was colorless) and dried in a vacuum oven at 50° C. for 6 hrs. The slightly hygroscopic product was a yellowish powder, weight 61.2 g (yield 61%), m.p. 244°-246° C.

HPLC Analysis: the product was analyzed against 7-chloroquinalidne from Trans World Chemicals, both dissolved in 10/90 $CH_3CN$/0.1% $H_3PO_3$. Purity: 98.8% wt. HPLC conditions: Zorbax RX-C8 4.6 mm×25 cm column, 10/90 $CH_3CN$/0.1% $H_3PO_4$ solvent, 1.5 mL/min flow, detector at 223 nm wavelength. Retention time: 7-chloroquinaldine 8.0 min, 5-chloroquinaldine 12.7 min. Relative peak ratio of 7- vs. 5-chloroquinaldine 99.75% to 0.25%.

$^1$H NMR in $CD_3OD$ confirmed the structure.

EXAMPLE 2

Effects of Added Oxidants

Syntheses essentially the same as in Example 1 were run using various oxidants other than chloranil. The effects on yield are shown in Table 2-1. For the syntheses of the first column, crotonaldehyde addition took 5-10 minutes. For the second column synthesis the addition took 50 minutes.

TABLE 2-1

Effects of Added Oxidants

| Added Oxidant | 7-Chloroquinaldine Yield (%)* | |
|---|---|---|
| | 5-10 min. | 50 min. |
| None (Control) | 42 | |
| FeCl₃ | 55 | |
| CuCl₂ | 49 | |
| 3-Nitrobenzenesulfonic acid, sodium salt | 42 | |
| 3-Chloronitrobenzene/cat. FeCl₃ | 42 | |
| 2,3-Dichloro-5,6-dicyano-1-4-quinone | 58 | |
| 1,4-Benzoquinone | 53 | |
| 9,10-Anthraquinone | 42 | |
| o-Chloranil | 59-66 | |
| p-Chloranil | 67 | 81 |

*Determined by gas chromatography

What is claimed is:

1. An improved process for preparing 7-chloroquinaldine by reacting 3-chloroaniline with crotonaldehyde wherein the improvement comprises:
   1) running the reaction in a non-aqueous medium,
   2) catalyzing the reaction with a mineral acid dissolved in alcohol, and
   3) using chloranil as an oxidant.
2. The process of claim 1 wherein the chloranil is p-chloranil.
3. The process of claim 1 wherein the alcohol is 2-butanol.
4. The process of claim 1 wherein the mineral acid is HCl.
5. The process of claim 1 wherein the crotonaldehyde is added to 3-chloroaniline and chloranil over a period of 0.5 to 2 hours.
6. The process of claim 1 further comprising:
   4) crystallizing said 7-chloroquinaldine as the HCl salt.

* * * * *